(12) United States Patent
Akman et al.

(10) Patent No.: US 8,562,349 B2
(45) Date of Patent: Oct. 22, 2013

(54) DENTAL IMPLANT THAT INCREASES BONE SUPPORT

(76) Inventors: Serhan Akman, Konya (TR); Mustafa Tunali, Ankara (TR)

( * ) Notice: Subject to any disclaimer, the term of this patent is extended or adjusted under 35 U.S.C. 154(b) by 54 days.

(21) Appl. No.: 12/811,007

(22) PCT Filed: Dec. 24, 2008

(86) PCT No.: PCT/TR2008/000145
§ 371 (c)(1),
(2), (4) Date: Jun. 28, 2010

(87) PCT Pub. No.: WO2009/085023
PCT Pub. Date: Jul. 9, 2009

(65) Prior Publication Data
US 2010/0285428 A1 Nov. 11, 2010

(30) Foreign Application Priority Data
Dec. 27, 2007 (TR) .............................. a 2007 09040

(51) Int. Cl.
*A61C 8/00* (2006.01)
(52) U.S. Cl.
USPC .......................................... 433/174; 433/173
(58) Field of Classification Search
USPC ............... 433/172–176, 201.1; 606/604, 323, 606/326, 328, 102; 411/383, 384, 393; 623/13.14
See application file for complete search history.

(56) References Cited

U.S. PATENT DOCUMENTS

| 5,899,696 | A | | 5/1999 | Shimoda | |
|---|---|---|---|---|---|
| 6,126,662 | A | * | 10/2000 | Carmichael et al. | 606/916 |
| 6,142,782 | A | * | 11/2000 | Lazarof | 433/174 |
| 6,309,220 | B1 | * | 10/2001 | Gittleman | 433/173 |
| 6,332,778 | B1 | * | 12/2001 | Choung | 433/173 |

FOREIGN PATENT DOCUMENTS

| WO | 99/37230 A1 | 7/1999 |
|---|---|---|
| WO | 00/21455 A1 | 4/2000 |

* cited by examiner

*Primary Examiner* — Yogesh Patel
(74) *Attorney, Agent, or Firm* — Bayramoglu Law Offices, LLC

(57) ABSTRACT

A dental_implant that increases the amount of bone around the implant by increasing its length in order to place a longer implant without the need for a sinus elevation surgery in the posterior maxillary region where bone stock is not sufficient by employing the principles of displacement procedures in implantology which rely on regeneration of patient's own bone and have been used for years in the dentistry for orthodontic procedures. The dental implant has a pressure adaptor that protrudes and advances through the apical part of the implant body. Pressure adaptor is advanced within the bone until desired length of implant and bone is achieved. This procedure forms significant amount of bone around the implant within the floor of maxillary sinus. Floor of maxillary sinus is elevated. New bone is formed without the need for an additional surgery.

3 Claims, 5 Drawing Sheets

DENTAL IMPLANT THAT INCREASES BONE SUPPORT

FIELD OF THE INVENTION

The present invention relates to the field of dental implants, and in particular to an implant with a pressure unit to form bone construction around the implant.

BACKGROUND OF THE INVENTION

Dental implants are biocompatible functional devices that are placed into bones for substituting an extracted tooth or providing support to fixed or mobile prostheses. The goal of implant design is to provide sufficient initial stability and accomplish osteointegration as early as possible after implantation. Implants are kept load-free for 3 to 6 months following primary surgery. During this period, new regular bone that will stand against the occlusive loads is formed around the implant (osteointegration); so the implant becomes stable enough to resist functional forces created during mastication. Following this stage, prosthetic restoration is done onto the implant to obtain a functional implant.

Magnitude of mechanical stress on alveolar bone depends on the diameter and length of the implant; proper placement of implants with respect to the direction of the forces applied; the number of implants and distribution of the forces. Increasing length of the implant increases its load-bearing surface. Increased length is also crucial for primary stability. Implant should resist shearing and torque forces when abutment is mounted. Increased length also reduces the stress applied on the neck of the implant. Implant body design, screw geometry and surface characteristics are continuously being improved to strengthen the implant-tissue interface, and to attain ideal load transfer; eventually to increase the success and survival of the implant.

High number of anatomic spaces and important nerves in the oral region limits the length of the implants to be used and mandates a detailed examination. If occlusive forces are increased, larger and longer implants should be used. However, confined width and length of the bone restricts the use of implants with appropriate length and width. This negatively affects the long-term success of the implant.

SUMMARY OF THE INVENTION

Sagging of the sinus floor, insufficient height and quality of bone are common problems in the patients that have remained toothless for a long time particularly in the posterior maxillary region, and it is rarely possible to place an implant of sufficient length in proper position. Even if the implant can be placed, this situation causes the implant to have bone support with poor quality. We have inspired from the displacement technique that is based on regeneration of the patient's own bone and widely used in the dentistry for orthodontic procedures to place a long implant to the maxillary posterior region without the need for sinus lifting where bone distance is particularly insufficient; and by using this technique in implantology we aimed to increase the amount of bone around the implant by increasing its length.

Throughout the normal development of the root of the teeth, increased root length is associated with increased length of alveolar bone. This physiologic and remarkably slow mechanism allows growth of roots to sufficient length without jeopardizing important structures such as maxillary sinus or inferior alveolar nerve. In a similar manner, the implant we have designed can be gradually lengthened to allow the use of an implant of sufficient length in areas with insufficient bone length.

BRIEF DESCRIPTION OF THE DRAWINGS

The present invention will be apparent to those skilled in the art by reading the following description of preferred embodiments thereof, with reference to the attached drawings, in which.

DETAILED DESCRIPTION

Figure 1:
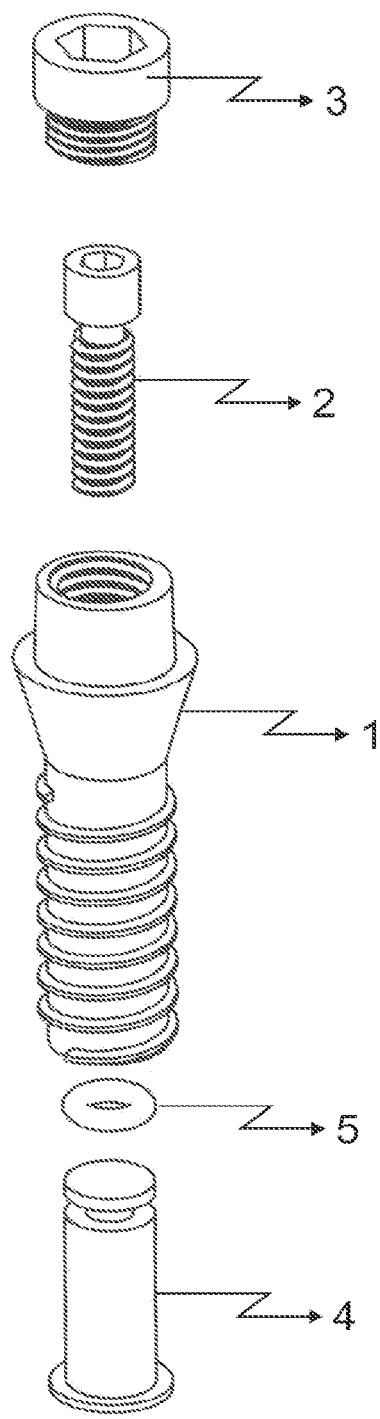
FIG. 1 is a view of the implant system
Figure 2:
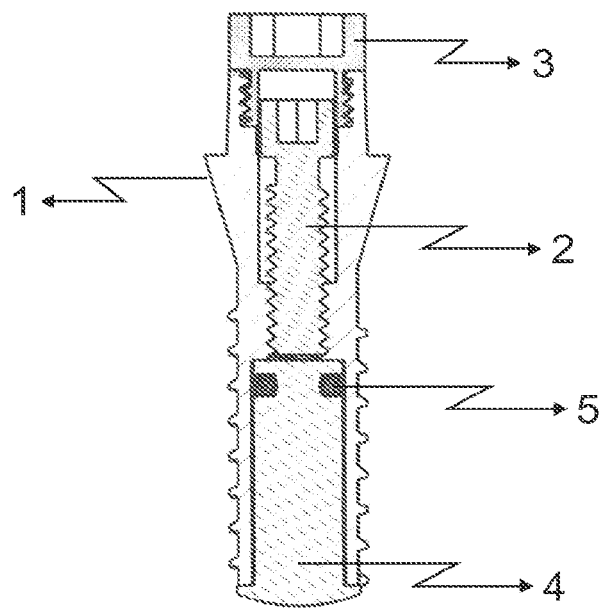
FIG. 2 another view of the implant system
Figure 3:
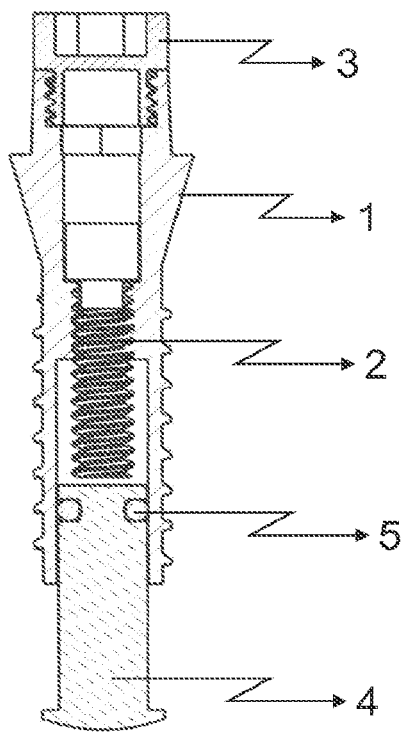
FIG. 3 is a view showing the relationship between the screw and the pressure unit
Figure 4:
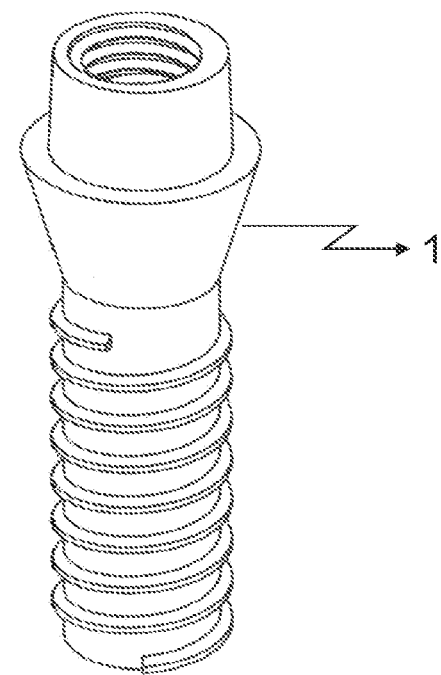
FIG. 4 is a view of the pressure screw
Figure 5:
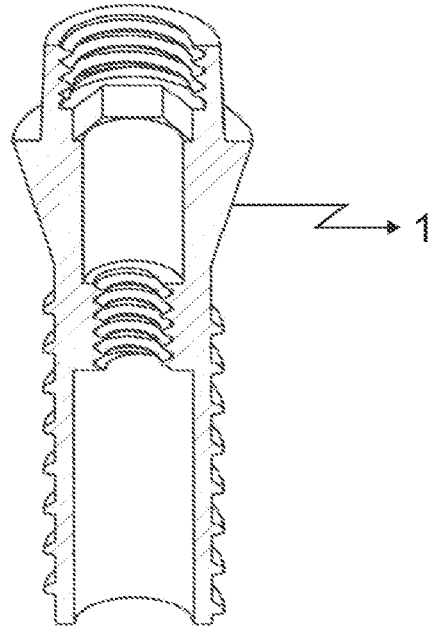
FIG. 5 is a view showing the relationship between the pressure screw and the pressure unit

The implant system we have designed consists of 5 parts (FIG. 1, 2, 3, 4, 5). In the implant system, there is a pressure adaptor (4) that protrudes and advances through the apical part of the implant body (1). Following insertion of implant system into the posterior maxillary area and attainment of osteointegration (FIG. 6), driving screw (2) is used to force the pressure adaptor (4) of the implant system into the floor of the sinus (FIG. 7). Force applied within physiologic limits initiates remodeling around the terminal part of the pressure adaptor (4) similar to the behavior of the bones of the teeth that are exposed to orthodontic forces. This process is carried on until a desired implant and bone length is achieved. Implant system also contains a leak-proof element (5) that prevents leakage between pressure adaptor and the implant body. A screw cap (3) is mounted on the implant body to prevent immigration of bacteria and foreign bodies from the oral cavity. These all lead to significant bone formation around the implant system within the maxillary sinus floor. Floor of maxillary sinus is elevated (FIG. 7). New bone is formed without the need for an additional surgical procedure.

Figure 6:
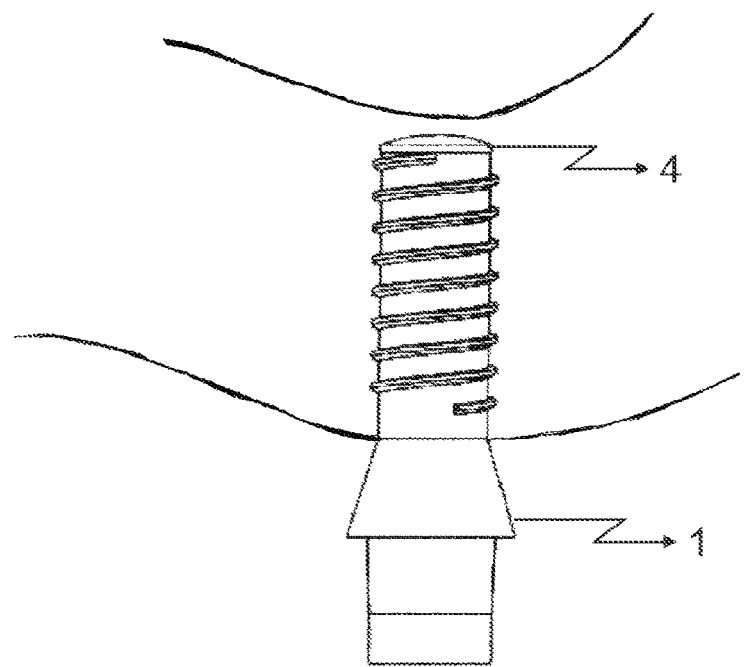
FIG. 6 is a view of the implant located in the bone adjacent to the sinus floor
Figure 7:
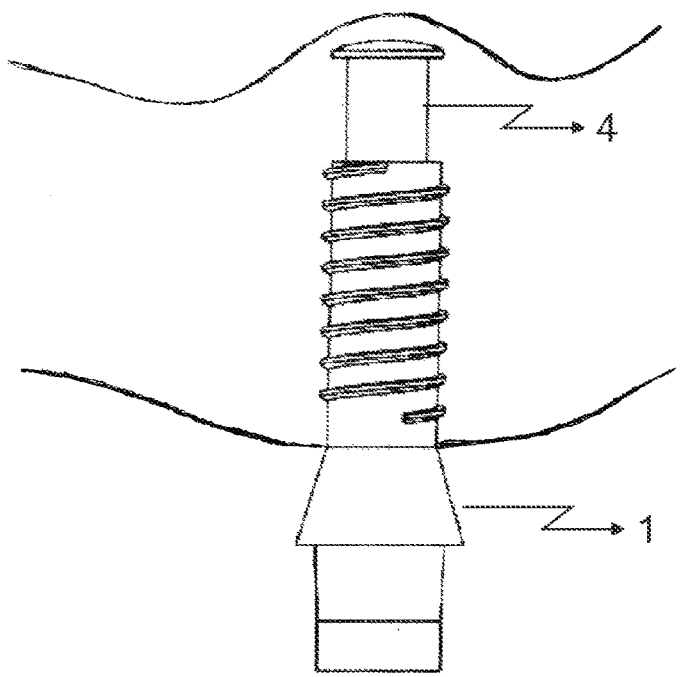
FIG. 7 is a view of the pressure unit protruding and pushing on the bone

Our newly developed implant system provides new bone formation by bone remodeling (FIG. 6, 7). Unlike the implant distractors that make use of distraction osteogenesis by forming fracture on the bone and make use of flexible fracture callus to form new bone, this implant system make use of remodeling without creating a fracture. Bone formation through remodeling is much slower. This implant system offers a higher patient acceptance as it requires no additional surgery and is less traumatic compared to distractors.

Figure 8:
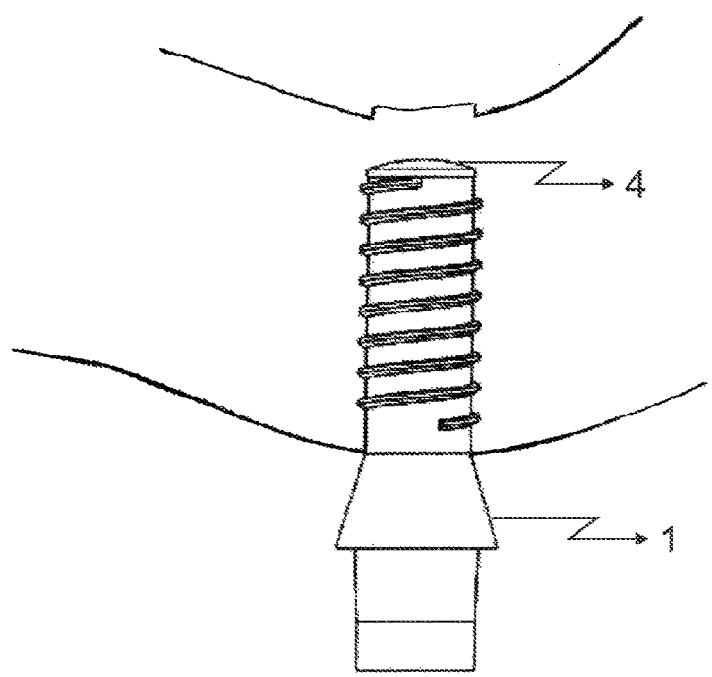
FIG. 8 is another view of the pressure unit pushing on the bone
Figure 9:
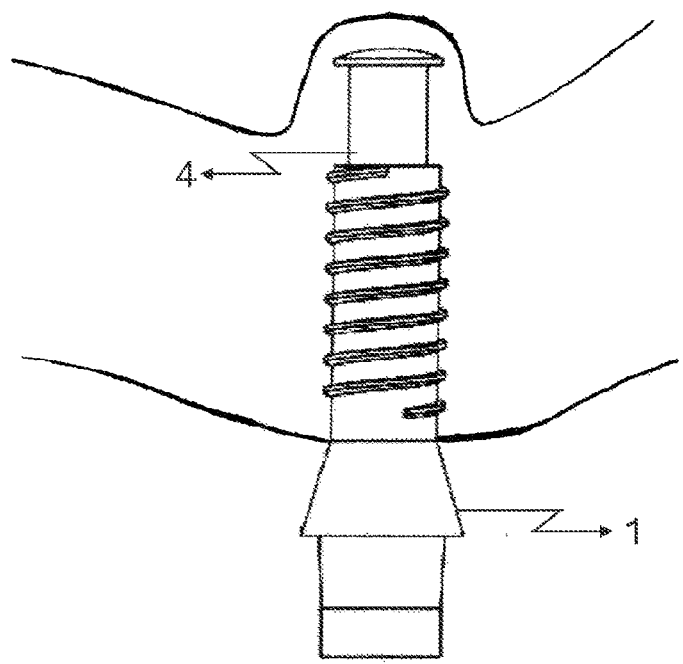
FIG. 9 is a view showing the pressure unit further pushing into the bone

However, by unique application different from the other distractors, this implant system can also be used for distraction osteogenesis in maxillary sinus or other anatomic spaces (FIG. 8, 9). Unlike other distractor implants which require osteotomy at the middle part of the implant, in this system only a minimal fracture is formed at the cortical bone above the apical part of the implant as presented in FIG. 8 to form callus and consequently new bone in a way similar to distraction osteogenesis. For this procedure, driving screw (2) is advanced and pressure adaptor (4) forces fractured part through the anatomic space fairly faster compared to remodeling (FIG. 9). In the distractor implants osteotomy line is at the middle part of the implant.

The invention claimed is:

1. A method of inserting a dental implant into a bone structure for formation of new bone structure around the implant, the implant comprising an implant body with a cavity in its apical section; a pressure adaptor that resides in the cavity of the implant body, wherein the pressure adaptor is capable of moving out of the cavity of the implant body; a pressure screw located in the body and it is in contact with the pressure adapter for applying force and pushing the pressure adapter out of the implant body when the pressure screw is rotated; wherein the pressure adaptor moves axially when a force applied to it by the pressure screw; a leak-proof element that is located between the pressure adapter and the apical section of the implant body;

the method comprising: making a hole in the bone structure; placing the implant into the hole generated in the bone; rotating the pressure screw and pushing outwardly the pressure adaptor therefore causing the pressure adaptor to move such that the pressure adaptor makes contact and applies pressure to the bone an implant cap that is mounted on the implant body after pushing the pressure adaptor.

2. The method of claim 1 wherein the process of pushing the pressure adaptor continues periodically by applying a rotating force to the pressure screw.

3. The method of claim 1 wherein the process of pushing the pressure adaptor continues until the desired implant and bone length is achieved.

* * * * *